(12) United States Patent
Barham

(10) Patent No.: US 8,353,305 B1
(45) Date of Patent: Jan. 15, 2013

(54) PRESSURE VESSEL FOR TREATING DENTURES

(76) Inventor: William L Barham, Mt. Airy, NC (US)

( * ) Notice: Subject to any disclaimer, the term of this patent is extended or adjusted under 35 U.S.C. 154(b) by 1338 days.

(21) Appl. No.: 11/657,255

(22) Filed: Jan. 24, 2007

(51) Int. Cl.
B01D 1/18 (2006.01)
A61C 17/00 (2006.01)

(52) U.S. Cl. ........................................................ 134/93
(58) Field of Classification Search ...................... 134/93
See application file for complete search history.

(56) References Cited

U.S. PATENT DOCUMENTS

| | | | |
|---|---|---|---|
| 2,196,566 A | | 4/1940 | Sabattis |
| 2,541,595 A | | 2/1951 | Marshall et al. |
| 2,973,767 A | | 3/1961 | Cohen |
| 3,133,305 A | | 5/1964 | Revan-Rosenstock |
| 3,912,451 A | | 10/1975 | Gaglia, Jr. |
| 4,182,238 A | * | 1/1980 | Mitchell et al. ................. 100/99 |
| 4,251,007 A | | 2/1981 | Behnisch |
| 4,331,251 A | | 5/1982 | Berman et al. |
| 4,534,485 A | | 8/1985 | Subramanian |
| 4,724,855 A | * | 2/1988 | Jackson et al. ................. 134/93 |
| 4,750,610 A | | 6/1988 | Ryder |
| 4,857,224 A | | 8/1989 | Eoga |
| 4,996,027 A | | 2/1991 | Kanner |
| 5,184,718 A | | 2/1993 | Albert |
| 5,609,837 A | | 3/1997 | Cerny et al. |
| 5,729,956 A | | 3/1998 | McGlothlin |
| 5,756,044 A | | 5/1998 | Mowrey-McKee et al. |
| 6,213,777 B1 | | 4/2001 | Seitzinger |
| 6,217,933 B1 | | 4/2001 | Edwards et al. |
| 6,341,688 B1 | | 1/2002 | Graham |
| 6,386,358 B1 | * | 5/2002 | North et al. .................... 206/217 |
| 6,729,491 B2 | * | 5/2004 | Morris, Jr. ..................... 220/284 |
| 2002/0157985 A1 | * | 10/2002 | Edwards et al. ............... 206/524 |
| 2004/0136864 A1 | * | 7/2004 | Barham .......................... 422/27 |

FOREIGN PATENT DOCUMENTS

DE 19607237 * 8/1997

* cited by examiner

Primary Examiner — Michael Barr
Assistant Examiner — Jason Riggleman
(74) Attorney, Agent, or Firm — Robert W. Pitts

(57) ABSTRACT

A denture treating apparatus employs a receptacle base with a chamber closed by a rotatable cover. A denture and an effervescing denture treating composition, such as a denture cleaning tablet is place in water in the chamber. When the chamber is closed, the pressure created by the effervescing tablet causes the active ingredients to penetrate small spaces in the denture. A seal is compressed between relative thick peripheral lips on the cover and receptacle base. Thinner sections of the receptacle base can bow under pressure to show that pressure is building up. A shiftable handle on the cover makes it easier for a user to close the cover and compress the seal.

26 Claims, 7 Drawing Sheets

PRESSURE VESSEL FOR TREATING DENTURES

BACKGROUND OF THE INVENTION

1. Field of the Invention

This invention is related to the treatment of dentures and especially to more effectively cleaning or deodorizing dentures. This invention is also directed to the removal of biolayers that can build up in confined spaces within a denture and to the capability of denture treatment compositions to wet or contact confined areas where these biolayers can be deposited.

2. Description of the Prior Art

Many methods and techniques have been suggested to facilitate cleaning and disinfecting dentures. Denture cleaning can be broadly defined as the reduction of a biolayer or biofilm and plaque containing bacteria, fungi and virus and pathogens or debris in general. Generally some method is employed to disrupt the plaque coating or biolayer and to soak the denture to allow chemical solutions to interface with denture surface and with porosities, micro-channels, fissures, cracks, fractures and spaces between teeth and the acrylic that retains the teeth in the gum portion of the denture. Additional pores, micro-channels, fissures, cracks, and fractures can be formed as a denture ages or by scratching, by toothpaste abrasives, and bacterial action that pits the denture surface.

One common approach to cleaning dentures is to use effervescent tablets, which foam when placed in water. Conventional tablets contain cleaning agents. Traditionally, these tablets have a composition containing a variety of sulfate salts, such as bisulfates, monopersulfates and sulfates acting as detergents, oxidizers and the like. They have also used alkali metal and alkaline earth metal halides as bleaches. Such compositions have also included perborate, carbonate and phosphate salts in varying amounts to provide effervescence and activation. A discussion of some of these traditional effervescent cleaning compositions can be found in U.S. Pat. No. 4,857,224, which is incorporated herein be reference.

Limitations have been encountered with standard prior art methods. Strong solutions containing alcohol adversely affect the acrylic. Some cleaning or treatment solutions are too strong for biocompatibility with oral tissues. Microwaving weakens the dentures and may warp the acrylic due to uneven heat buildup. Mechanical means to scrap the denture surface are incomplete and the size of practical mechanical scraping means is too large to remove plaque in microscopic pores, micro-channels, fissures, cracks, and fractures. Furthermore mechanical means tend to scarify or abrade the denture surface thereby increasing fissures where pathogens may build up.

A method for improving the action of standard denture treatment compositions, such as denture cleaners, and an apparatus for use in practicing that method is disclosed in U.S. patent application Ser. No. 10/339,802 filed on Jan. 10, 2003. This pending patent application is entitled Treatment of Dentures at Elevated Pressures. The apparatus disclosed therein has demonstrated the efficacy of employing elevated pressures with standard denture cleaning and treating compositions. However, the apparatus depicted therein, has some practical problems. For instance, it can be difficult to maintain an adequate gas tight pressure seal in a relatively inexpensive pressure containment vessel suitable for use by the average consumer. The rigidity needed for surfaces compressing the seal introduces difficulties because of the limitations imposed by injection molding plastics for such a product. Also, the amount of force that may be needed to adequately compress a seal may be difficult to apply for elderly users who may have inadequate grip strength. It is also important that the pressure generated by effervescent denture cleaning compositions not be lost by a failure to quickly seal the pressure chamber. The denture treatment, pressure containment vessel of the instant invention addresses these and other problems.

SUMMARY OF THE INVENTION

The denture treating apparatus according to this invention is primarily intended to improve the performance of a conventional denture cleaning tablet by employing a pressure tight container in which the conventional denture cleaning tablet is employed. Pressure in excess of ambient pressure is believed to promote additional penetration of the cleaning agent in a conventional denture treating tablet so that contaminants, especially contaminants located in crevices and confined spaces in a denture, will be more effectively exposed to active cleaning agents. According to the preferred embodiments of this invention, this excess pressure is developed by activation of a conventional denture cleaning tablet within a confined pressure chamber. Effervescence resulting from depositing such a conventional denture cleaning tablet in water can be relied upon to produce this enhanced pressure, but it has been found that to reliably generate effective pressures, the pressure containment vessel must employ a gas tight seal that will not leak when subjected to pressures on the order of ten (10) to twenty five (25) psi above ambient or atmospheric pressure. A practical pressure containment vessel suitable for use with a conventional denture cleaning tablet must not only be capable of maintaining pressures of this magnitude, but the pressure containment vessel must also be relatively inexpensive to produce and must be easy to open and close, especially by an elderly denture wearer. A pressure containment vessel in accordance with this invention is intended to be used by a typical denture wearer, and in order to be cost effective, it would need to be injection molded and mass marketed. However, it has been found that the combination of the required sealing performance with standard, relatively inexpensive manufacturing methods is difficult to achieve. The pressure containment vessel must be sealed and force must be evenly applied to a seal. It has been found that the top of the pressure containment vessel should be screwed to the receptacle base of the pressure containment vessel in order to evenly apply a force around the entire seal. If an effervescent denture cleaning tablet is employed it is also necessary to quickly close the chamber or cavity before significant amounts of gas escapes. It has also been determined that the surface supporting a seal cannot be deformed when pressure is applied by screwing the two vessel components together. Otherwise it would be difficult to maintain intimate contact between a sealing gasket and the surfaces abutting the sealing gasket. Furthermore a gasket forming the seal must have sufficient lubricity to allow the vessel to be closed with an even pressure distribution. Since most denture wearers are elderly, the pressure vessel needs to be configured so that it can be closed by users who may possess less than average strength and may find it difficult to apply the force necessary to maintain an adequate seal. These requirements impose somewhat contradictory limitations of a denture treatment apparatus having the desired capabilities.

A denture treating apparatus according to one embodiment of this invention and possessing characteristics sufficient to overcome the enumerated and other difficulties encountered in the development of this apparatus, includes a cover that can be mounted on a receptacle base to enclose a pressure containment chamber or cavity. The receptacle base forms the majority of this chamber, which has an open end at the top of the receptacle base so that the chamber can be filled with water or some other fluid. The receptacle base includes a receptacle base peripheral lip extending around the open end of the chamber. The cover can be secured to the receptacle base over the open end of the chamber, to close the chamber. The cover includes a cover peripheral lip opposed to the receptacle base peripheral lip when the receptacle base is secured to the open end of the chamber. A seal is positioned between the receptacle base peripheral lip and the cover peripheral lip. The cover can be rotated relative to the receptacle base to compress the seal to form a pressure tight chamber in which a denture can be treated or cleaned. The receptacle base comprises a one-piece molded member including a cylindrical outer wall and a bottom wall. The cylindrical outer wall is thicker in a section forming the receptacle base peripheral lip than in a section forming the bottom wall. The thin wall extends over the majority of the receptacle base and are easier to fabricate, but the thicker peripheral lip provides a surface, which will not excessively deform under pressure while in engagement with the seal. The cover can have also employ a relatively thick cover peripheral lip compressing the seal. A relatively thinner receptacle base bottom section can bow outward under pressure to show a user that an effective pressure is being developed within the gas tight chamber. Also a relatively thinner bottom section will relieve stress that would otherwise tend to deform the sealing rim.

A denture treating apparatus, that can be closed by a user who may not possess normal grip strength employs handles on the cover and the receptacle base. One handle is attached to the cover and engages the cover to twist the cover relative to the receptacle base to open and close the chamber. This handle is shiftable relative to the cover between multiple positions to improve the ease of manipulating the handles to close the cover. The cover handle imparts rotation in opposite directions to open and close the chamber.

The cover of this apparatus may also include a holder in which a denture treatment tablet may be mounted prior to introducing the tablet into water in the receptacle base chamber. In this way an effervescing tablet will only begin to emit gas as the cover encloses the chamber, and gas will not be lost before the chamber is closed. Effective pressure can then be more reliably developed by an inexperienced user.

DETAILED DESCRIPTION OF THE PREFERRED EMBODIMENTS

The denture treating apparatus 2 according to the preferred embodiment of this invention can be employed to treat dentures. Normally vessel 2 would be employed to clean a denture using any one of a number of commercially available standard denture cleaning tablets. This invention can be employed to improve the effectiveness of standard effervescent denture cleaning tablets including both cleaning and foaming agents. Conventional tablets, such as Efferdent denture cleaning tablets and Polident denture cleaning tablets could be employed. Efferdent is a trademark of Warner-Lambert and Polident is a trademark of Glaxo Smith Kline. Use of this pressure enhanced denture treatment apparatus 2 is not limited to use of these commercially available compositions. Other treatments, including cleaning, disinfecting, deodorizing, brightening, bleaching or other compositions could also be employed. For example, the treatment agent could include menthol or eucalyptus oil. Other treatment agents could include, but would not be limited to, cetylpyridinum chloride, chlorhexidiene gluconate, eugenol, clove oil or peppermint oil. Chlorine dioxide could be used as the active agent and as the foaming agent for denture treatment in a dentist's office. As this compound dissociates the chlorine would provide the anti-bacterial agent and the oxygen would increase the pressure within the pressure containment vessel. Other simple foaming agents could also be employed. For example, baking soda and a salt could be used to make the water acidic to release carbon dioxide. In other words, both the materials and the pressure containment structures disclosed herein are merely intended to be representative, and other compositions and mechanical components would be readily apparent to one of ordinary skill in the art. It is believed that this pressure treating vessel would also increase the effectiveness of virtually any denture cleaning or treating solution because the added pressure will disperse the active ingredient into tight spaces in the denture where pathogens or bacteria might not otherwise be exposed to active denture treating or cleaning agents. A pressure treating apparatus according to this invention would therefore even improve the effectiveness of new denture or dental treating agents that may not be currently be commercially available or may not as yet have been developed.

Figure 1:
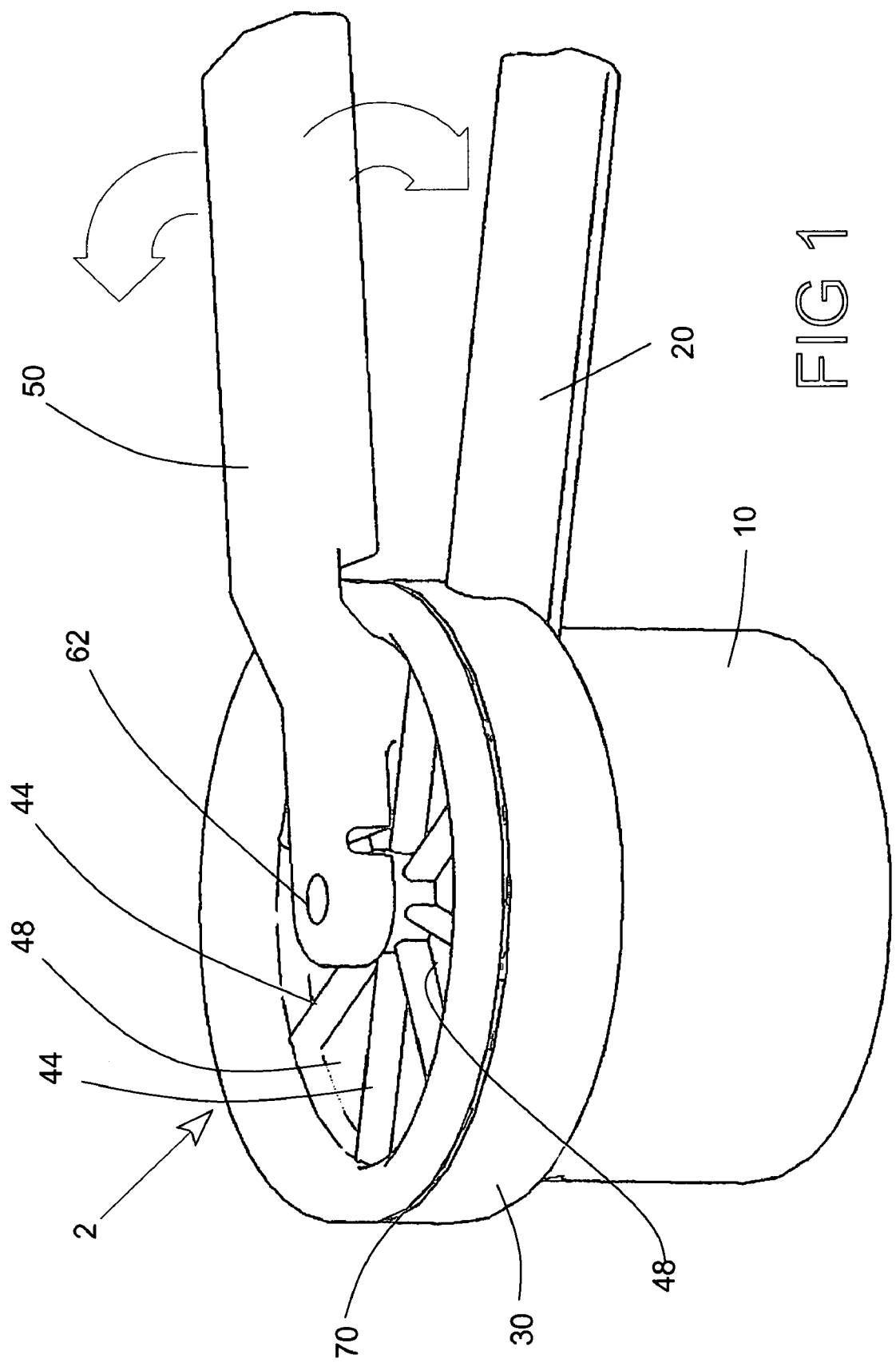
FIG. 1 is a view of a pressure treatment vessel according to this invention showing a cover mounted on a receptacle base.
Figure 2:
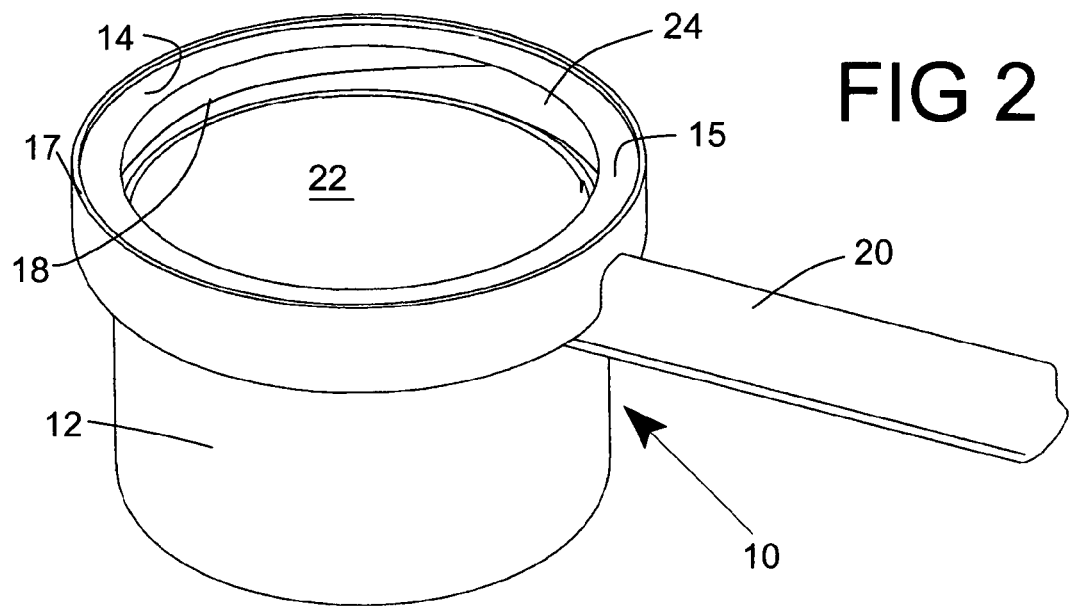
FIG. 2 is a view of the receptacle base comprising one part of the vessel of FIG. 1

As shown in FIG. 1, the denture treating apparatus or vessel 2 comprises a receptacle base 10 to which a cover 30 can be secured. The cover 30 can be screwed onto the receptacle base 10 to close a chamber 22, as shown in FIG. 2, formed within the receptacle base 10. A gasket seal 70 will be compressed between the cover 30 and the receptacle base 10 to provide a pressure tight seal that will prevent the passage of either liquids or gas. The cover 30 can be closed and opened by twisting the cover 30 relative to the receptacle base 10. A receptacle base handle 20 and a cover handle 50, both of which protrude radially from the main section of the denture treating vessel 2, provide sufficient mechanical advantage to allow the cover 30 to be closed tightly so that the gasket seal 70 can be compressed sufficiently to maintain a gas tight seal. This mechanical advantage is important because dentures 84 will normally be worn by older people, many of whom are not capable of exerting a great deal of force to close the chamber 22. The receptacle base handle 20 will preferably comprise an integral part of a one-piece molded receptacle base 10, and will therefore be rigid relative to the main cylindrical section of receptacle base 10. In the preferred embodiment of this invention, the cover handle 50 will be pinned to the cover 30 about a central pivot point 62 so that the cover handle 50 can be rotated relative to the cover 50, and when placed in the operative position shown in FIG. 1, the cover handle 50 can be rotated relative to receptacle base handle 20 to impart rotation of the cover 30 relative to the receptacle base 10. As will be subsequently discussed in greater detail, the cover handle 50 can be lifted and positioned, relative to receptacle base handle 20, so that the two handles are in a convenient position for closing or opening the chamber 22 by rotating the cover 20. Furthermore, the position of the cover handle 50 relative to the remainder of the cover 30 can be changed while the cover is partially closed or open if convenient.

Figure 3:
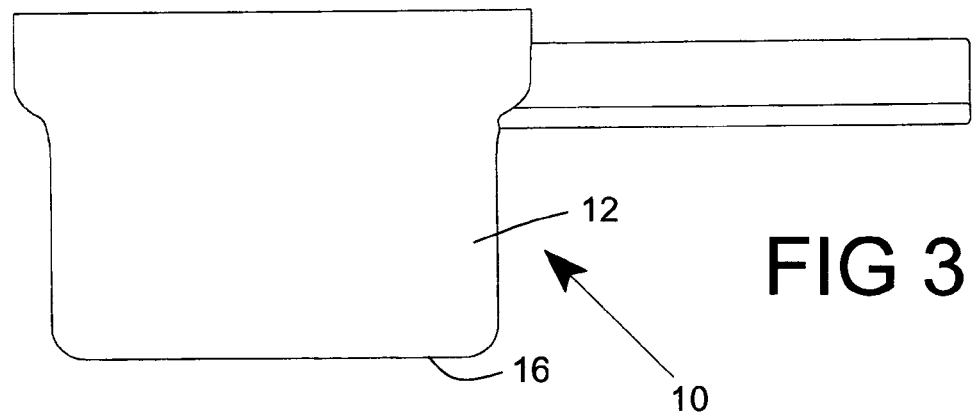
FIG. 3 is a side view of the receptacle base shown in FIG. 2.
Figure 4:
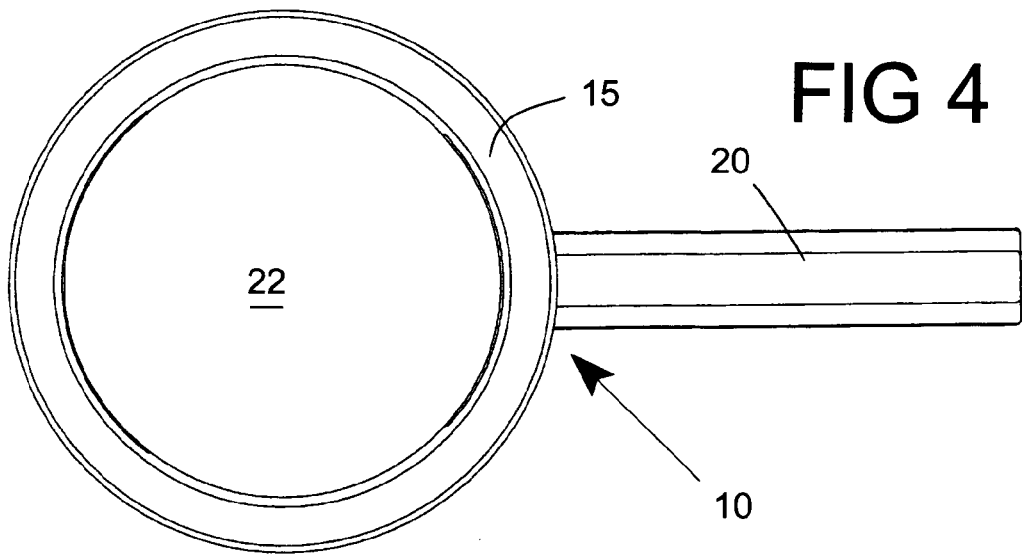
FIG. 4 is a top view of the receptacle base of FIGS. 1-3 showing the chamber formed in the receptacle base.
Figure 11:
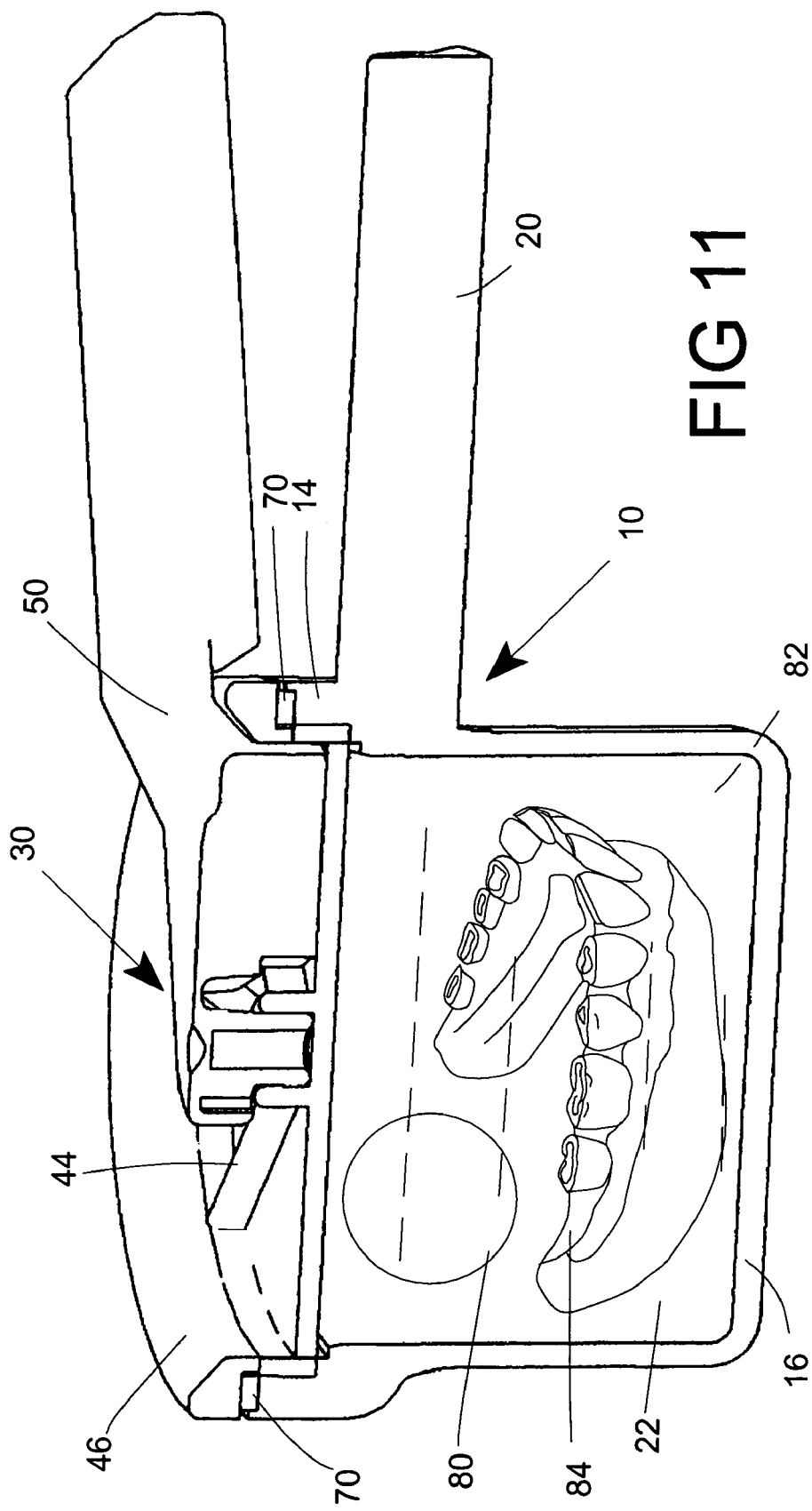
FIG. 11 is a cross sectional view of the vessel showing a sealed chamber and the water level and the manner in which a denture treatment tablet is introduced into the water.

FIGS. 2-4 show the receptacle base 10 in more detail. Receptacle base 10 can be injection molded employing a commonly available plastic resin, such as an acrylic. Other materials or manufacturing processes can be employed, but receptacle base 10 is especially adapted to be constructed using a straight pull, injection molding process so that the receptacle base 10 can be economically fabricated. The receptacle base 10 has sufficient strength so that a pressure of at least ten (10) psi above ambient pressure can be maintained within chamber 22. The chamber 22 is generally cylindrical in shape and is defined by a receptacle base cylindrical outer wall and a flat bottom wall 16 that closes the bottom of chamber 22. An open upper end 24 has an inner diameter equal to the inner diameter of the remainder of the chamber 22. Although limited to one particular size, one representative embodiment of receptacle base 10 employs a chamber having a volume of three hundred to five hundred (300-500) cubic centimeters. The volume of the chamber 22 is sufficient to receive a denture 84 or dentures, a denture cleaning tablet and sufficient water with which the denture cleaning tablet will react to effervesce so that pressure can build up in the chamber 22. FIGS. 2, 3 and the cross section of FIG. 11 illustrate that the thickness of the cylindrical outer wall 12 varies between the bottom wall 16 and the open chamber end 24. A thicker peripheral lip section 14 is formed adjacent the upper open chamber end 24. This thicker lip section forms an upwardly facing ledge 15 that is surrounded by an even thinner receptacle base rim 17. As will be subsequently discussed in more detail, the peripheral lip 14 and the ledge 15 will support a gasket seal 70. The thickness of the peripheral lip 14, which will form a continuous toroidial structure, will be sufficient to prevent deformation of the peripheral lip and ledge 15 when the chamber 22 is pressurized to at least ten (10) psi relative to ambient pressure. A dimensionally stable lip 14 is important for maintaining a gas tight seal with a simple gasket seal 70 of the type employed herein. In one representative embodiment, the thickness of peripheral lip 14 can be approximately five (5) to six (6) mm. In the preferred embodiment of this invention, a three hundred and sixty screw (360) degree thread 18 is formed on the interior of the peripheral rim 14.

The thickness of the remainder, or lower part, of cylindrical outer wall 12 and of bottom wall 16 is less than the thickness of the peripheral lip 14. One reason for employing thinner wall sections 12 and 16 is to reduce the amount of material needed to fabricate the receptacle base 10 and to reduce the cycle time for molding these parts. A thinner wall section will also cool quicker, and should prevent formation of flaws or warping in the plastic as it cools. A thinner base section will also tend to relieve stress in the base that might otherwise tend to deform the sealing rim. Although it would be possible to fabricate the entire receptacle base 10 with a thickness equal to the thicker peripheral lip 14, the fabrication would be more difficult and expensive. In one representative embodiment of this invention, the thickness of the cylindrical wall 12 and the bottom wall 14 would be 3 mm.

In addition to these practical advantages for using thinner wall sections, there is one functional advantage to employing thin bottom wall 16. A thinner bottom wall will be more flexible than a thicker wall. Although dimensional stability is important for the peripheral lip 14, it is not critical for the bottom wall, provided of course that the thickness of the bottom wall 16 is sufficient to maintain the required pressure in chamber 22. With a thinner wall, the bottom can bow outward when the chamber 22 is pressurized. The thickness of the bottom wall 16 can be chosen so that this outward deformation is noticeable when an effective pressure is developed within chamber 22. If an initially flat bottom wall 16 bows outwardly, the vessel 2, under pressure, will not longer sit flat on a horizontal surface. The user can then tell if an effective pressure has been developed in chamber 22 and if the denture treatment apparatus is functioning properly. A simple level-detecting device may even be added on the exterior of the receptacle base 10, so that a user can easily detect if the device continues to function properly.

Figure 5:
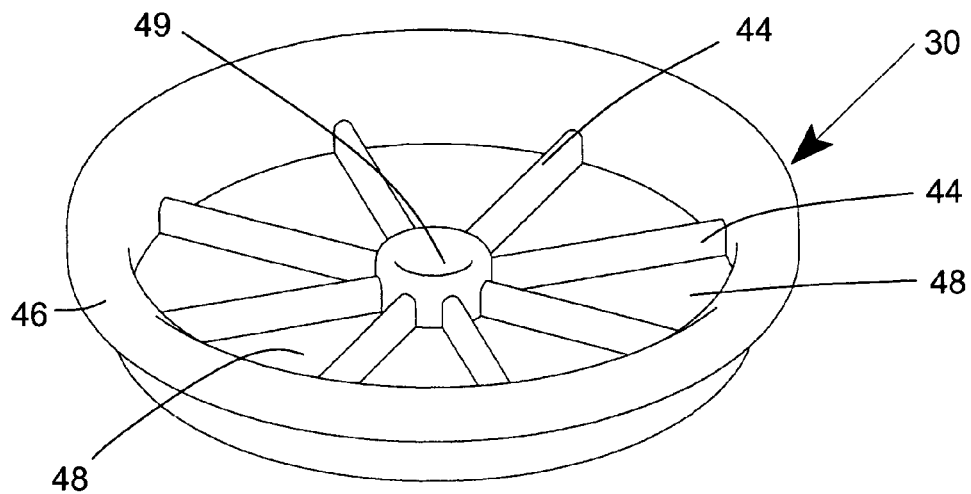
FIG. 5 is a view of the cover mountable on the receptacle base.
Figure 6:
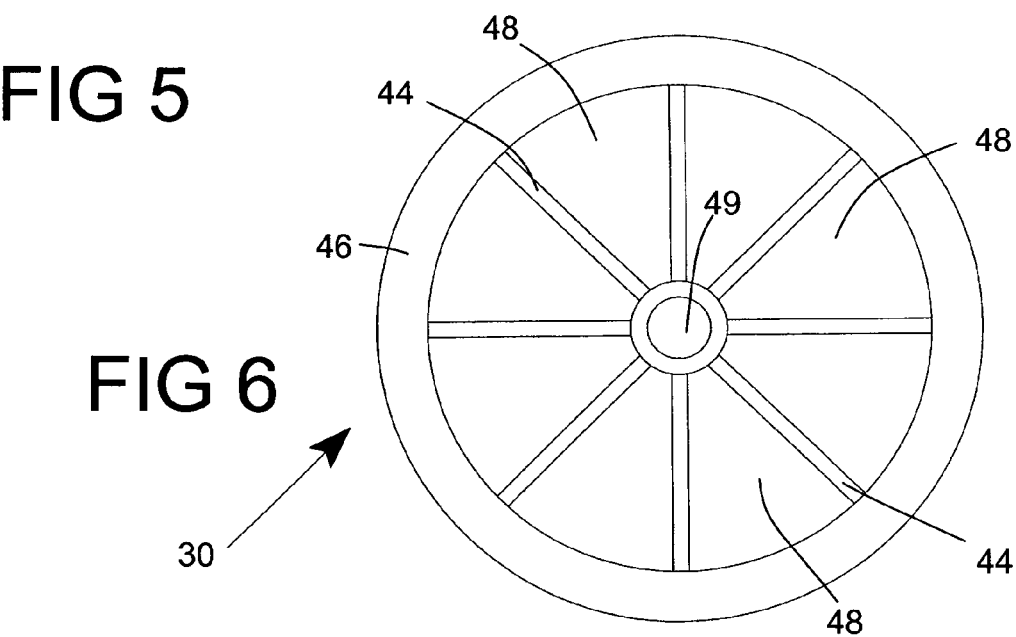
FIG. 6 is a top view of the cover showing radially extending strengthening ribs.

A representative embodiment of the cover 30 is shown in FIGS. 5 and 6. The cover 30 includes a disk section 32 with an annular wall 34 extending around the periphery of the disk 32. The exterior face 38 of cover 30 faces upward and an interior face 40 faces downward and will form the upper surface of the chamber 22 when closed. A cover peripheral lip 46 extends outwardly from the annular wall 34 and forms a downwardly facing ledge 45, which will engage a gasket seal 70, which will be positioned between the cover ledge 45 and the receptacle base ledge 15 when the cover 30 is mounted on the receptacle base 10. The cover peripheral lip 46 has a thickness that is greater than the thickness of the annular wall 34 or the cover disk 32, and the cover peripheral lip 46 will not deform when the chamber 22 is pressurized. A plurality of strengthening ribs 44 radiate outwardly from the center of the cover disk 32 to the cover peripheral lip 26 and a series of pie shaped segments 48 are formed between the strengthening ribs 44. A hub 49 is formed at the center of the radiating strengthening ribs 44. The center of this hub 49 can be removed or taped so that a cover handle 50 may be mounted on the cover 30. The cover 30, including the disk 32, the annular wall 34, the peripheral lip 42 and the strengthening ribs 44 can be molded as an integral one-piece member. Threads 36 may be formed on the exterior of the annular wall 34. Cover threads 36 will mate with receptacle base threads 18, when the cover 30 is twisted onto or off of the receptacle base 10. Threads 36 extend completely around the annular wall 46 for 360 degrees for continuous engagement around the pressure containment cavity or chamber to avoid warping.

Figure 7:
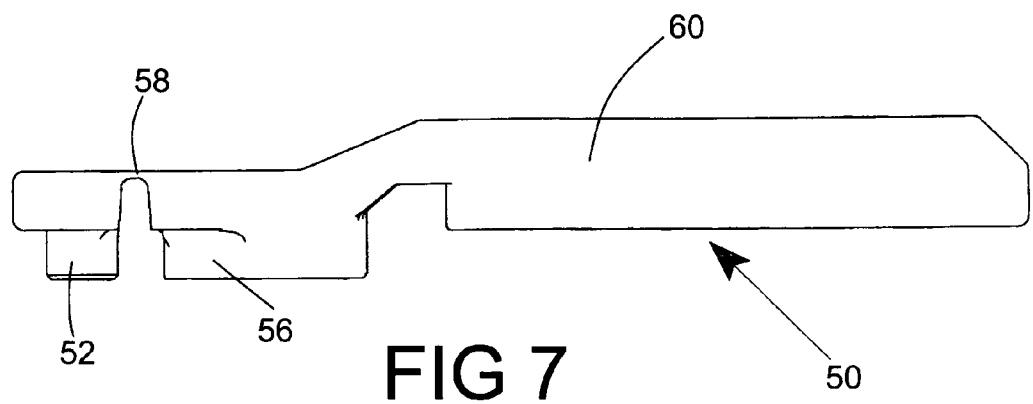
FIG. 7 is a side view of the cover handle.
Figure 8:
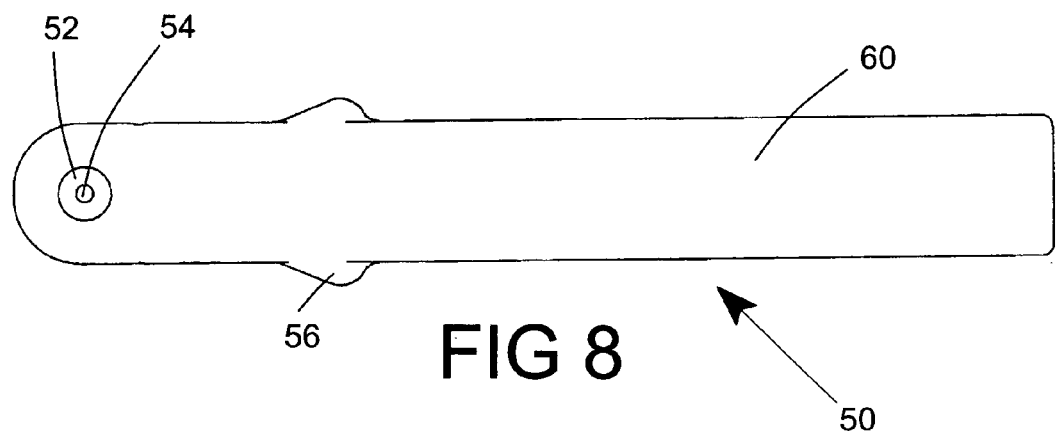
FIG. 8 is a top view of the cover handle.
Figure 9:
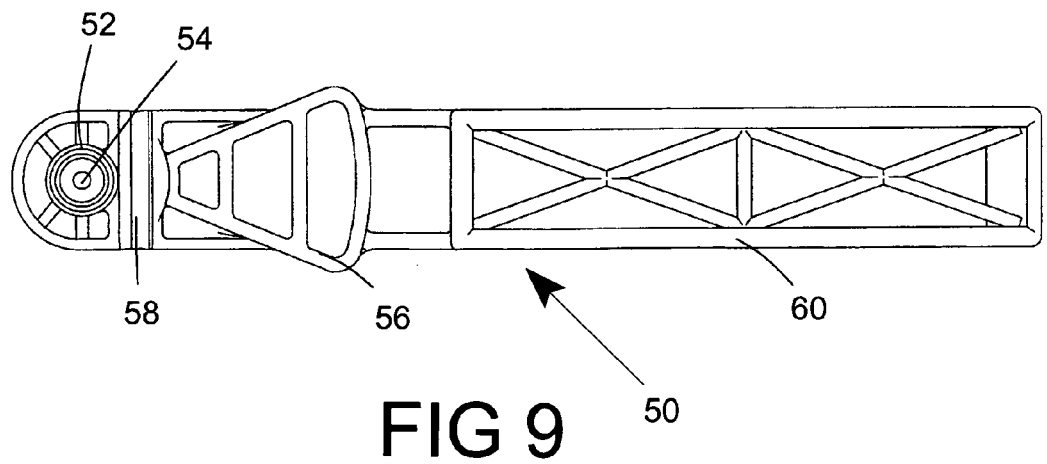
FIG. 9 is a bottom view of the cover handle.

The cover handle 50 is molded separately from the cover 30, and the cover handle 50 is subsequently attachable to the cover 30 at a center pivot point 62. Details of cover handle 50 are shown in FIGS. 7-9. Cover handle 50 can be injection molded as a one-piece component. Cover handle 50 includes a center post 52 that is employed to mount the handle 50 to the hub 49 at the center of the cover 30. As shown in the cross sectional view of FIG. 11, a hole 54 extends upwardly from the bottom of the center post 52. As molded this hole 54 is closed at one end, but when a tapping screw is used to attach that cover handle 50 to the cover, the tapping screw will puncture the closed section and will extend through hole 54.

The mechanical advantage provided by the handles 20 and 50 is also important because the lubricity of the seal may be adversely affected by the action of the denture cleaning tablet, making it otherwise difficult to open the cover 30. Not only must the gasket seal 70 have sufficient lubricity to permit opening and closing, and be capable of withstanding a pressure differential, but the vessel 2 still must be opened after the denture is cleaned, even if there are adverse effects on the seal 70 over time.

A relatively thin section is formed next to the center post 52 and this thin section will form a flexible hinge 58 between the center post 52 and a wedge section 56. The sides of the wedge section 56 are tapered so that the wedge section 56 can fit in any one of the segments 48 defined between the strengthening ribs 44 on cover 30. A grip section 60 extends outwardly from the wedge section 56. This hinge 58 is sufficiently flexible and has enough clearance so that the cover handle can be rotated upwardly by a sufficient distance so that the wedge section 56 can clear the cover strengthening ribs 44. The cover handle 50 can then be rotated about the center pivot point 62 so that the wedge section 56 can be inserted in any of the segments 48. When the handle 50 is returned to its normal position, the wedge section 56 will fit within the selected segment and will engage the sides of strengthening ribs 44. Rotation of the shiftable cover handle 50, in either the clockwise or counterclockwise direction will twist the cover 30 relative to the receptacle base 10, which remains stationary because the user is simultaneously gripping receptacle base handle 20. Angular adjustment of the cover handle 50 in this manner makes it easier to orient the cover handle 50 relative to the receptacle base handle 20 so that it will be easier to twist or rotate the cover 30 between the closed and open positions. This will be of special importance when a user, who may have arthritic hands or may have lost grip strength, attempts to close the cover and compress the seal 70. He or she can choose the most convention orientation of the cover handle 50 relative to the receptacle base handle 10, and can even adjust the cover handle 50 is a ratchet-like fashion when manipulating the cover 30.

Figure 10:
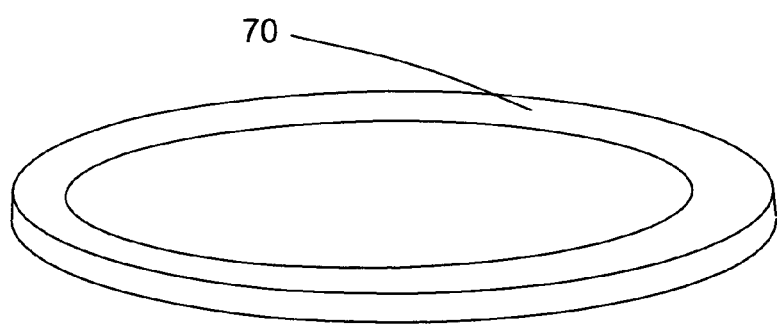
FIG. 10 is a view of the gasket seal.

A gasket seal 70 is shown in FIG. 10. This seal 70 comprises an annular elastomeric member that will be compressed as the cover 30 is screwed onto the receptacle base 110. Gasket seal 70 has a flat cross section and can be fabricated from a material such as silicone or Teflon impregnated flexible acrylic. It should be understood that seals having other shapes, such as a circular cross section, could be employed, but it has been found that a seal having the configuration shown in FIG. 10 is both economical and effective. The cover 30 is screwed to the receptacle base 10 by mating screw threads 18 that extend completely around the periphery of both the receptacle base 10 and the cover 30 so that an essentially uniform pressure will be applied to compress the gasket seal 70.

Compression of the gasket seal between the cover 30 and the receptacle base will to some extent reduce the volume of the chamber 22. The cover 30 acts as a press. Once the bottom of the gasket seal 70 fully engages the flat ledge 14, under pressure produced by screwing in the cover 30, the fluid in the chamber 22 is trapped and pressure within the chamber 22 begins to increase due to the effervescence of the cleaning tablet. As the cover 30 is screwed tighter, the gasket seal 70 is flattened. Approximately 2 to 3 psi can be generated by flattening the gasket seal 70. Thus a mechanical means can be employed to increase the pressure within and enclosed chamber, and to some extent the effectiveness of a denture treating agent in the chamber can be enhanced. A thicker gasket seal 70 would result in even greater pressure, but continued compression of the gasket seal 70 can result in extra drag, making it more difficult to open and close the cover 30. The lip 17 extending around the periphery of the ledge 17 will, however, trap or capture the gasket seal 70 and will resist excessive compression of the gasket seal 70, and will therefore limit damage to the seal 70 as well as preventing excessive drag, which would make it more difficult for a user, especially an elderly user to open and close the vessel.

FIG. 11 is a cross sectional view of the denture treating apparatus 2 showing the assembled components, including the receptacle base 10, the cover 30, the cover handle 50 and the seal 70. For illustrative purposes the tapping screw attaching the cover handle 50 to the cover 30 is not shown. The cover 30 and the cover handle 50 are shown in their "as molded" state. It should be understood that a tapping screw or other means can be employed to puncture the closed portion of the center handle post 52 and puncture the cover within the hub 49 to hold the center post 52 on the center pivot position so that the cover handle can rotate relative to the cover as previously discussed. As shown in FIG. 11, the receptacle base peripheral rim 14 and the cover peripheral rim 46 are both relatively thick in comparison to the remaining sections of the receptacle base 10 and the cover 30. These rims are therefore relatively rigid and are not subject to deformation when pressure is generated within chamber 22. The ledges 15 and 45, engaging opposite flat sides of gasket seal 70 will therefore not deform and will uniformly compress the gasket seal 70 resulting in a gas tight as well as a fluid tight seal that can withstand a pressure of at least ten (10) psi. relative to ambient pressure on the exterior of the vessel 2.

Figure 12:
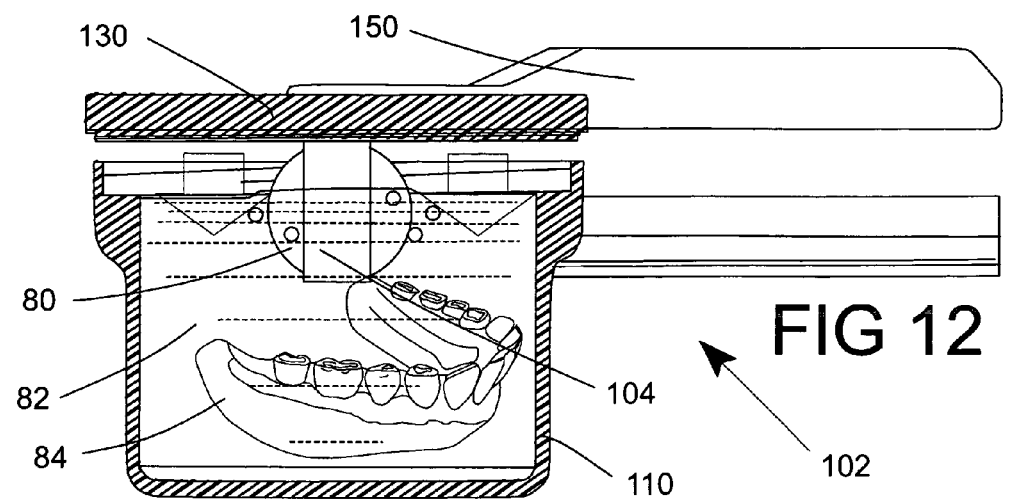
FIG. 12 is a cross sectional view of an alternate embodiment of a denture treating apparatus in which a holder on the interior surface of the cover retains a denture cleaning tablet.
Figure 13:
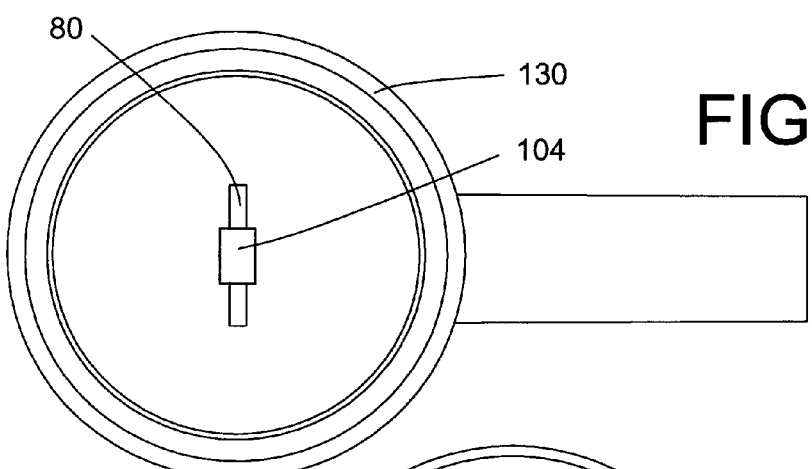
FIG. 13 is a view of the interior surface of the cover of the embodiment of FIG. 12.
Figure 14:
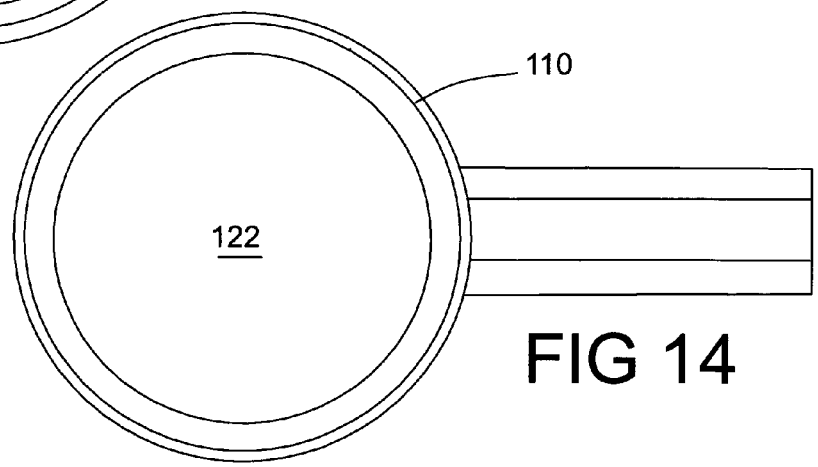
FIG. 14 is a view of the receptacle base and the open chamber of the embodiment of FIGS. 11 and 12.

An alternate embodiment of this invention is shown in FIGS. 12-14. That denture treating vessel 102 employs a cover 130 that includes a holder 104 mounted on the interior face of the cover 130. This holder 104 comprises a strap that is large enough to hold a partially exposed denture treatment tablet 80. Conventional denture treatment tablets can have a diameter of approximately one (1) inch and a thickness of approximately one-tenth (0.1) inch. The holder 104 could be a rigid molded plastic member or an elastomeric member bonded to the cover 130. A denture treatment tablet 80 can be inserted into holder 104 before the cover 130 is placed onto a receptacle base 110 in which the chamber 122 has been previously filled with water 82. The denture treatment tablet 80 will then enter the water 82 only as the cover 130 is placed on the receptacle base. The cover 130 can then be quickly screwed onto the receptacle base 110. Almost no gas effervescing from the tablet 80 (as illustrated by the bubbles shown in FIG. 12) after it has been placed in the water 82 will escape the vessel 102, and there will be little chance that sufficient overpressure is not developed in the enclosed chamber 122. FIG. 12 shows an embodiment in which the holder is positioned so that the denture treatment tablet 80 is in an upright position. In this way, at least a portion of the tablet 80 will enter the water 82, even if the chamber 122 is not filled to the top. In that eventuality, the remainder of the tablet 80 would subsequently drop into the water as the reaction proceeds.

Figure 15:
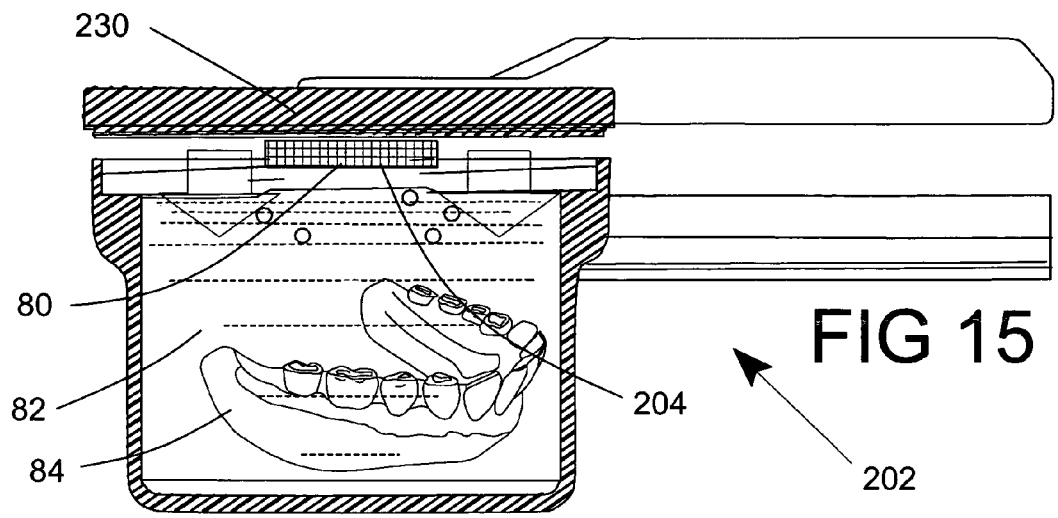
FIG. 15 is a cross sectional view showing another alternative approach to positioning a denture cleaning tablet on the apparatus cover.
Figure 16:
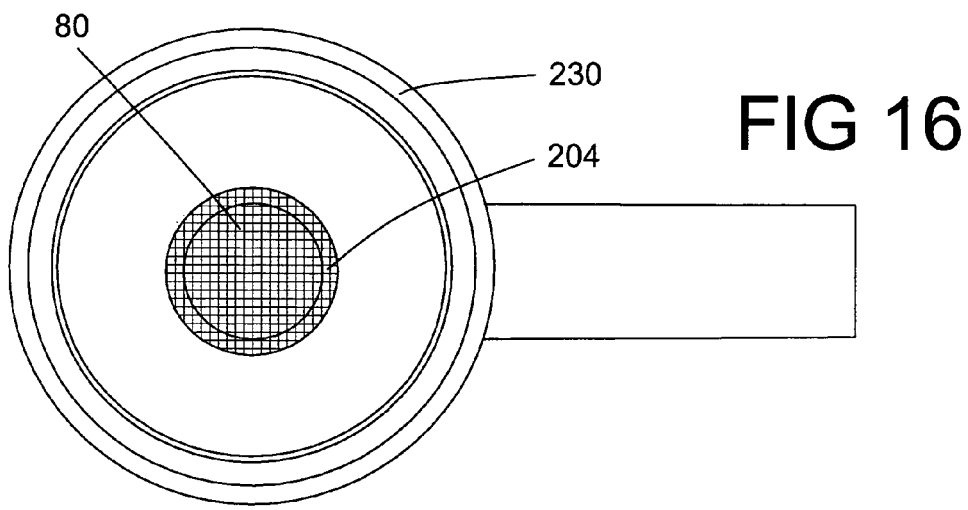
FIG. 16 is a view of the interior surface of the cover of the embodiment of FIG. 15.

A second alternative embodiment is shown in FIGS. 15-16. This denture treating vessel 202 employs a cover 230 that includes a basket 204 mounted on the interior face of the cover 230. This basket 204 has an opening on its side so that a denture treating tablet 80 can be inserted into the basket 204 and can be positioned so that its circular faces extend parallel to the interior face of the cover 230. The thickness of basket 204 is only slightly larger than the thickness of the denture treating tablet 80. In this position, the denture treating tablet 80 will not enter and react with until cover 230 is almost completely closed. There will therefore be less escape of gas emanating from the reaction of the denture treating tablet 80 and water before the cover 230 is closed than with the first two embodiments. Although the upper face of the tablet 80 may initially be flush with the interior cover face, and therefore not completely exposed to the water, the denture treatment tablet will progressively dissolve and the entire tablet will be fully exposed to the water in the chamber.

Figure 17:
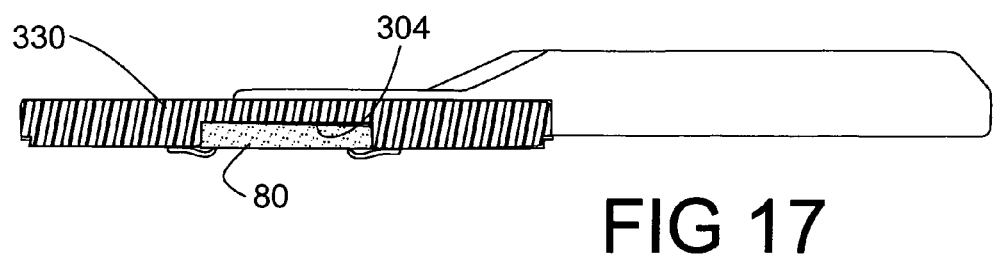
FIG. 17 is a view of a third embodiment in which the tablet is positioned within a recess in the cover.

FIG. 17 shows still another alternate embodiment. In this version, the cover 330 includes a recess 304 extending inwardly from the interior face of cover 330. This recess is sized so that a denture treatment tablet 80 can be located in recess 304, before the tablet 80 is even partially immersed in water. Clips or other conventional means can be employed to retain the denture treatment tablet 80 in recess 304. The bottom surface of the tablet 80 is substantially flush with the bottom surface of the cover 330. With this version the tablet 80 will not enter the water until after the treads on the cover 330 engage the treads on the mating base, which would have the same shape, as base 10 or base 110. Thus the pressure chamber would be closed before the tablet 80 entered the water. Since there would be insufficient time to develop substantial amount of effervescence, there would be even less gas lost as the cover 330 is secured to the base, resulting in the possibility of an even greater pressure rise, once the pressure chamber has been sealed.

The alternate embodiments of FIGS. 12-17 show modifications to the manner in which the table will be introduced into the water. The embodiment of FIGS. 12-14 includes a cover handle 150 that is an integral part of the one-piece cover 130. It should be understood, however, that a shiftable cover handle, such as cover handle 50 employed with the embodiment of FIGS. 1-11, could also be used with these alternate embodiments. A denture treatment apparatus incorporating both a shiftable cover handle 50 and a holder 104 would have the advantages of each component, and the shiftable cover handle 50 is not shown in FIGS. 12-17 in order not to complicate the views of these alternate embodiments.

Of course these alternate representative embodiments are not the only options for implementing this invention. For example, other configurations employing primarily mechanical means to reduce the volume of the chamber could be employed to increase the pressure. Other modifications would be apparent to those of ordinary skill in the art, without departing from the invention disclosed herein. It is the claims and not the specific representative embodiments, which define this invention.

I claim:

1. A denture treating apparatus comprising:
   a receptacle base forming a chamber with an open end, the receptacle base including a receptacle base peripheral lip extending around the open end with an upwardly facing surface on the receptacle base peripheral lip;
   a cover, securable to the receptacle base over the open end of the chamber, to close the chamber, the cover including a cover peripheral lip opposed to the receptacle base peripheral lip when the receptacle base is secured to the open end of the chamber;
   a seal positioned on the upwardly facing surface of the receptacle base peripheral lip between the receptacle base peripheral lip and the cover peripheral lip; wherein the cover can be rotated relative to the receptacle base to compress the seal to form a pressure tight chamber in which a denture can be cleaned; and wherein
   the receptacle base comprises a one-piece molded member including a cylindrical outer wall and a bottom wall, the bottom wall being narrower than the section of the cylindrical outer wall forming the receptacle base peripheral lip, and with the upwardly facing surface on which the seal is positionable having a minimum width that is greater than the thickness of the bottom wall, so that deformation under pressure occurs in the bottom wall and not in the vicinity of the seal to maintain seal integrity under pressure.

2. The denture treating apparatus of claim 1 wherein the chamber can be sealed to retain a sufficient pressure to outwardly deform the bottom wall.

3. The denture treating apparatus of claim 2 wherein the receptacle base peripheral lip is not substantially deformed relative to the bottom wall when pressure is developed in the chamber.

4. The denture treating apparatus of claim 1 wherein a section of the cylindrical outer wall of the receptacle base is thicker than an adjacent section of the cylindrical outer wall joining the bottom wall.

5. The denture treating apparatus of claim 1 wherein the seal comprises a gasket seal.

6. The denture treating apparatus of claim 1 wherein the cover comprises a molded member including strengthening ribs extending along an exterior face to impart rigidity to the cover when the chamber is pressurized.

7. The denture treating apparatus of claim 1 wherein the cover is screwed into engagement with the receptacle base to close the chamber, with the seal closing a peripheral gap between the cover and the receptacle base and applying uniform pressure to the seal around the peripheral gap to seal the peripheral gap, the peripheral gap forming the only path between the chamber and the exterior environment surrounding the denture treating apparatus.

8. The denture treating apparatus of claim 1 wherein the cover comprises a flat disk with an annular wall extending upwardly to form a peripheral edge of the flat disk and a peripheral lip at the top of the annular wall.

9. The denture treating apparatus of claim 8 wherein the bottom wall of the receptacle base is parallel to the cover disk in the absence of pressure in the chamber in excess of ambient pressure, the bottom wall bowing outward relative to the cover disk when excess pressure is developed in the chamber.

10. The denture treating apparatus of claim 1 including a holder on an interior wall of the cover, the holder comprising means for retaining a denture treating tablet for introduction into the chamber, while in the holder.

11. The denture treating apparatus of claim 1 wherein the seal engages the cover and the receptacle base to form both a liquid tight and a gas tight seal so that excess pressure can be developed in the chamber when a denture treating tablet is introduced into water in the chamber.

12. The denture treating apparatus of claim 1 wherein the cover includes a cover peripheral lip having a thickness greater than the remainder of the cover to impart relative rigidity to the cover peripheral lip, the seal being positioned between the receptacle base peripheral lip and the cover peripheral lip when the chamber is closed.

13. A denture treating apparatus comprising:
   a receptacle base forming a chamber with an open end;

a cover, securable to the receptacle base over the open end of the chamber, to close the chamber; and a peripheral seal positioned between the cover and the receptacle so that pressure in the chamber can exceed ambient pressure for treating a denture placed in the chamber; wherein one of the receptacle base or the cover includes a section that is outwardly deformable when the pressure in the chamber is sufficient to improve performance of a denture treatment disposed in the chamber, wherein the deformable section is remote from the peripheral seal to limit leakage past the seal and portions of the receptacle base or the cover adjacent to the peripheral seal and between the peripheral seal and the deformable section are relatively stiffer than the deformable section.

14. The denture treating apparatus of claim 13 wherein the deformable section is outwardly deformable in the presence of a pressure within the chamber of at least ten psi greater than ambient pressure.

15. The denture treating apparatus of claim 13 wherein the deformable section comprises a section of one of the cover or the receptacle base that is thinner than sections of the cover and the receptacle base in engagement with the seal.

16. The denture treating apparatus of claim 15 wherein the deformable section comprises at least a portion of a bottom wall of the receptacle base forming a portion of the chamber.

17. A denture treating apparatus comprising:
a receptacle base forming a chamber with an open end;
a cover, securable to the receptacle base over the open end of the chamber, to close the chamber; and
a handle, attachable to the cover, and engaging the cover to twist the cover relative to the receptacle base to open and close the chamber, the handle being sequentially shiftable in a first direction relative to the cover after attachment thereto between multiple positions to sequentially impart rotation at each position to close the cover, the handle also being sequentially shiftable in a second direction relative to the cover after attachment thereto to sequentially impart rotation to open the.

18. The denture treating apparatus of claim 17 wherein the handle and the cover are attached to each other at a central pivot and the handle includes a flexible hinge, spaced from the central pivot, flexing of the hinge permitting the handle to shift between the first and second positions to permit rotation of the handle.

19. The denture treating apparatus of claim 18 wherein a seal is located between the cover and the receptacle base, so that the handle may be rotated to twist the cover and compress the seal to form a pressure tight enclosed chamber.

20. The denture treating apparatus of claim 17 wherein a plurality of ribs protrude from an exterior face of the cover, the handle engaging the ribs to impart rotation to the cover relative to the receptacle base.

21. The denture treating apparatus of claim 20 wherein the ribs form a series of segments, recessed relative to the ribs, on the exterior face of the cover, the handle being shiftable and insertable into segments between the ribs.

22. The denture treating apparatus of claim 21 wherein a second handle extends from the receptacle base, the handle on the cover being shiftable relative to the second handle and insertable into different segments to angularly space the handles relative to each other for twisting the cover relative to the receptacle base to further compress the seal.

23. The denture treating apparatus of claim 22 wherein the handle includes a tapered wedge insertable into segments formed by ribs diverging from a center of the cover to a peripheral edge of the cover.

24. The denture treating apparatus of claim 20 wherein the ribs comprise strengthening ribs.

25. The denture treating apparatus of claim 20 wherein the cover includes a peripheral rim, with the ribs extending between a central point on the cover to the peripheral rim.

26. The denture treating apparatus of claim 25 wherein the cover comprises a one-piece molded member and the handle comprises a separate molded member attachable to the cover only at a central pivot point.

* * * * *